United States Patent
Nomura et al.

(10) Patent No.: US 6,365,635 B1
(45) Date of Patent: *Apr. 2, 2002

(54) ANTIBACTERIAL COMPOSITION FOR TOPICAL ADMINISTRATION CONTAINING ANTIBIOTIC

(75) Inventors: Masaaki Nomura; Hiromi Sumikawa; Osamu Sugita, all of Gunma-ken (JP)

(73) Assignee: Suntory Limited, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/380,530

(22) PCT Filed: Jan. 12, 1999

(86) PCT No.: PCT/JP99/00068

§ 371 Date: Sep. 2, 1999

§ 102(e) Date: Sep. 2, 1999

(87) PCT Pub. No.: WO99/36098

PCT Pub. Date: Jul. 22, 1999

(30) Foreign Application Priority Data

Jan. 13, 1998 (JP) .......................... 10-004845

(51) Int. Cl.$^7$ .................. A61K 47/32; A61K 31/43; A01N 25/00
(52) U.S. Cl. ............. 514/772.4; 514/192; 424/405
(58) Field of Search .............. 514/192, 220, 514/772.4, 412, 421, 413, 529; 424/405

(56) References Cited

U.S. PATENT DOCUMENTS

| 4,272,437 A | 6/1981 | Menard et al. |
| 4,282,150 A | 8/1981 | Menard et al. |
| 4,692,442 A | 9/1987 | Gosteli et al. |
| 4,701,320 A | 10/1987 | Hasegawa et al. |
| 4,743,598 A | * 5/1988 | Ganguly et al. |
| 4,997,829 A | 3/1991 | Ishiguro et al. |
| 5,116,832 A | 5/1992 | Ishiguro et al. |
| 5,354,748 A | * 10/1994 | Sugita et al. |

FOREIGN PATENT DOCUMENTS

| EP | 0788801 A1 | 8/1997 |
| JP | 54-119486 | 9/1979 |
| JP | 56-25111 | 3/1981 |
| JP | 60-222486 | 11/1985 |
| JP | 61-130228 | 6/1986 |
| JP | 61-207387 | 9/1986 |
| JP | 62-123120 | 6/1987 |
| JP | 63-162694 | 7/1988 |
| JP | 4-13616 | 1/1992 |
| JP | 6-227964 | 8/1994 |
| JP | 7-89847 | 4/1995 |

OTHER PUBLICATIONS

Woodward, R.B.; The chemical Society; London, Spec. No. 28, 1997, p. 167–180, "Recent Advances in the Chemistry . . .".
Kagaku Ryoho no Ryoiki, vol. 13 No. 10, 1997, p. 74–80.
Chemotherapy vol. 42, S–1, 1994, p. 38–50.
Japanese Journal of Chemotherapy (Nihon Kagaku Rhyoho Gakkai Zasshi), vol. 45 No. 11, 1997, p. 965–971.

* cited by examiner

Primary Examiner—Thurman K. Page
Assistant Examiner—Blessing Fubara
(74) Attorney, Agent, or Firm—Nixon & Vanderhye

(57) ABSTRACT

The present invention provides a safe antibacterial composition for topical administration which stably contains a penem antibiotic having a broad-spectrum and potent antibacterial activity while otherwise being chemically susceptible to hydrolysis, oxidation, photoisomerization or the like. The compositions of the present invention comprise an antibacterial composition for topical administration comprising a penem antibiotic or a pharmaceutically acceptable salt thereof in a non-aqueous base.

7 Claims, No Drawings

ANTIBACTERIAL COMPOSITION FOR TOPICAL ADMINISTRATION CONTAINING ANTIBIOTIC

This application is a 35 U.S.C. §371 of PCT/JP99/00068 filed Jan. 12, 1999.

FIELD OF THE INVENTION

The present invention relates to pharmaceutical compositions for use in dermatological, ophthalmologic, otolaryngologic, dental/oral surgical and urogenital fields, and more specifically to the use of penem antibiotics for topical administration.

PRIOR ART

Ointments are used for topical administration to treat various diseases due to their convenience of administration and portability.

Therapeutic agents comprising antibiotics in an ointment base are useful for treating local inflammatory or pyogenic diseases caused by bacterial infection. There is a demand for these ointments, with a number being available.

For example, ointments containing aminoglycoside, tetracycline and chloramphenicol antibiotics are commonly used for inflammatory or pyogenic diseases in dermatological, ophthalmologic, otolaryngologic, dental/oral surgical and urogenital fields. Specific examples include commercially available dermatological agents for pyogenic diseases, based on aminoglycoside antibiotics such as kanamycin monosulfate ointments, tetracycline antibiotics such as tetracycline hydrochloride ointments and chloramphenicol antibiotics such as chloramphenicol ointments, as well as commercially available ophthalmic ointments based on macrolide antibiotics such as pimaricin formulations. Ointments containing tetracycline hydrochloride as a tetracycline antibiotic and hydrocortisone acetate are commercially available for dental/oral surgical application.

The active component in antibiotic ointments should be incorporated in a stable form. Japanese Patent Publication (Kokoku) No. 12728/89 describes a composition for topical administration as an external dental agent. In this composition, a magnesium compound is employed to a hydrogel comprising minocycline or a pharmaceutically acceptable salt thereof as a tetracycline antibiotic in a water-soluble polymer compound and a polyhydric alcohol to stabilize the antibiotic.

On the other hand, penem compounds are non-natural β-lactam compounds designed based on the concept of combining the structures of penicillin and cephalosporin (e.g. see Woodward, R. B., In Recent Advances in the Chemistry of β-Lactam Antibiotics; Elks, J., Ed; The Chemical Society; London, 1977; Spec. No. 28, pp. 167–180, Japanese Patent Public Disclosure (Kokai) Nos. 207387/86, 162694/88, 222486/85 and 119486/79), with the aim of creating a new range of antibiotics which have the broad antibacterial spectrum and high safety of penicillin antibiotics and cephem antibiotics belonging to β-lactam antibiotics combined with the potent antibacterial activity and high stability to β-lactamase of carbapenem antibiotics.

Currently, sodium (+)-(5R, 6S)-6-[(R)-1-hydroxyethyl]-7-oxo-3-[(R)-2-tetrahydrofuryl]-4-thia-1-azabicyclo[3.2.0]hepto-2-ene-2-carboxylate 2.5 hydrate (faropenem sodium, hereinafter referred to as Compound 1) is orally administated as a therapeutic agent for use in various infections. The penem compounds are reported to show potent antibacterial activity on not only methicillin-sensitive *Staphylococcus aureus* (MSSA), *Streptococcus pyrogenes* and *Streptococcus pneumoniae* but also gram-positive bacteria less susceptible to conventional β-lactam agents such as penicillin-resistant *Streptococcus pneumoniae* (PRSP), stomatic Streptococcus spp. and Enterococcus sp. by virtue of the novel skeleton called penem ring. The broad-spectrum antibacterial activity covers gram-negative bacteria such as *Haemophilus influenzae* and anaerobics such as the genus Bacteroides (Antibiotics & Chemotherapy, Vol. 13, No. 10, pp. 74–80, 1997). They are also reported to exhibit potent antibacterial activity on not only pathogenic bacteria of periodontitis such as *Porphyromonas gingivalis* (Chemotherapy, Vol. 42, S-1, pp. 38–50, 1994) but also other strains which are becoming increasingly resistant, that cause dental infections (Chemotherapy, Vol. 45, No. 11, pp. 965–971, 1997).

However, penem compounds, like other β-lactam compounds, are generally chemically labile to hydrolysis, oxidation, photoisomerization, etc., and no composition for topical administration has been known that exhibits their excellent efficacy against inflammatory or pyogenic diseases, or diseases caused by infection with resistant bacteria.

Furthermore, in formulating ointments, an active component has to be mixed homogeneously throughout a semisolid base. When an active component is in the form of crystals or a crystalline powder like penem antibiotics, it is difficult to achieve overall homogeneity simply by dispersing the component in a base. Therefore, the component must first be ground into fine particles or dissolved in solvent, before being kneaded with a base into an ointment. Pulverization of the component is necessary also in view of the resulting texture of the formulation.

However, no technique for use of a penem compound as a component of an ointment has hitherto been known.

SUMMARY OF THE INVENTION

Under the circumstances described above, the inventors conducted extensive studies to develop a method to topically administer penem antibiotics and pharmaceutically acceptable salts thereof which have a broad-spectrum and a potent antibacterial activity as well as being highly safe. As a result, the inventors have developed a highly safe antibacterial composition for topical administration in which the active component is incorporated in a stable form. The present invention has been accomplished based on the finding.

Accordingly, the present invention relates to an antibacterial composition for topical administration comprising a penem antibiotic or a pharmaceutically acceptable salt thereof incorporated in a non-aqueous base.

According to the present invention, very unstable penem antibiotics can be stably incorporated in a non-aqueous base such as hydrophobic polymer compounds to provide an antibacterial composition which can be widely used in dermatological, ophthalmologic, otolaryngologic, dental/oral surgical and urogenital fields.

Antibacterial compositions of the present invention may further contain various additives such as water-soluble or hydrophilic polymer compounds conferring thickening effects to provide various compositions for intended uses without affecting the stability of active components.

DETAILED DESCRIPTION OF THE INVENTION

The composition of the present invention is basically a viscous liquid or paste-like composition comprising a penem antibiotic or a pharmaceutically acceptable salt thereof incorporated in a non-aqueous base, and it is typically formulated into an ointment. It is important that the base of a non-aqueous type is used to ensure the stability of the penem antibiotic.

Penem antibiotics used in the present invention are not specifically limited provided that they are antibacterially active, compatible to lesions and safe in view of irritability, sensitizing effect and oral toxicity, and that they are pharmaceutically acceptable. They may be either in the form of a free carboxylic acid or a pharmaceutically acceptable salt including salts with alkali or alkali earth metals such as sodium, potassium, calcium, magnesium or amino acids such as lysine or ammonium salts. Examples of such compounds other than the above Compound 1 include those in which the substituent at position 3 is 1,4-dioxane-2-yl, ethylsulphanyl, 3-tetrahydrofurylmethyl, methoxymethyl or ((aminocarbonyl)oxy)methyl or the like. The content of such a compound in the composition may be appropriately determined depending on the nature of the compound, the disease to be treated or other factors. For example, Compound 1 is incorporated at 10% by weight or less, normally 0.1 to 5% by weight expressed as free anhydride on the basis of the whole composition.

In order to formulate a penem antibiotic into an ointment, the active component must be incorporated into the composition in such a manner as to ensure the stability of the active component while assuring applicability or usability. In the present invention, proper stability can be ensured for penem antibiotics by using a non-aqueous base.

As used herein, "non-aqueous" base is a base which is substantially free from water. Thus, typical examples of non-aqueous bases are hydrophobic polymer compounds generally classified as hydrophobic ointment bases, such as oleaginous ointment bases consisting of hydrophobic polymers commonly used for ointments. Oleaginous ointment bases include, for example, hydrocarbon gel, paraffin, liquid paraffin, white petrolatum, petrolatum, microcrystalline wax, plant oils (vegetable oils), carnauba wax, beewax, stearic acid, stearyl alcohol, cacao butter, cetanol, hard fat, white ointment, simple ointment and ceresin.

Included in the non-aqueous bases used in the present invention are some emulsion bases which are free from any aqueous phase or film coating- or matrix -bases which are free from any aqueous phase. Emulsion ointment bases free from aqueous phase include hydrophilic petrolatum and purified lanolin. Film coatings and matrix bases free from any aqueous phase include acrylic resins which are commercially available under the trade name Eudragit (aminoalkyl methacrylate copolymer E, aminoalkyl methacrylate copolymer RS, methacrylic acid copolymer L, methacrylic acid copolymer S, ethyl acrylate.methyl methacrylate copolymer emulsion, available from Röhm Pharma, Germany) optionally in combination with plasticizers.

One or more of these bases are preferably used. Especially preferred are hydrocarbon gel, white petrolatum and Eudragit.

Neither hydrophilic bases in general nor many of the emulsion ointment bases, i.e. those comprising an aqueous phase, such as hydrophilic ointment and absorptive ointment will provide ointments which are capable of maintaining the activity of incorporated active components.

When the composition of the present invention is embodied as a pharmaceutical composition directly administered to a local site in the mouth for treating periodontitis, a high degree of viscosity will be required to provide a prolonged effect at the target site. In such a case, additives such as gelatinizers, thickening agents, viscosifiers, viscosity enhancers and elasticizers may be optionally added. Additives for this purpose include water-soluble or hydrophilic polymer compounds such as carmellose, carmellose sodium, polyvinyl alcohol, polyvinyl pyrrolidone, polyacrylic acid, sodium polyacrylate, hydroxymethylcellulose, hydroxypropylcellulose, hydroxypropylmethylcellulose, hydroxyethylcellulose, hydroxyethylmethylcellulose, xanthan gum, tragacanth gum, guar gum, locust bean gum, arabic gum, chitosan, sodium alginate, starches, gelatins, hydrophobically modified-hydroxypropylmethylcellulose (Sangelose, available from Sankyo Chemical). One or more of these compounds can be added at a proportion of 0.1 to 10% by weight, preferably 0.5 to 10% by weight on the basis of the whole composition to further enhance the thickening effect at the target site.

The water-soluble or hydrophilic polymer compounds may also be employed to facilitate the absorption of secreted fluids from body tissues and prevent any contamination at the location.

As long as the purposes and effects of the present invention are not compromised, other components such as conventional plasticizers, surfactants, perfumes, flavoring agents or other additives may be optionally employed in an amount which does not influence the stability of the active component.

Suitable plasticizers include triacetine, diacetyl ethylene glycol, diethyl sebacate, diethyl phthalate, dibutyl phthalate, diisopropyl adipate, dibutyl succinate. Suitable surfactants include polyoxyl stearate 40, polyoxyethylene hydrogenated castor oil, polyoxyethylene polyoxypropylene glycol, Polysorbate, sucrose esters of fatty acids. Suitable flavoring agents include sodium, saccharin or the like. Stabilizers such as calcium disodium edetate or the like may also be used as judged appropriate.

The composition of the present invention may further contain appropriate amounts of perfumes such as menthol, carboxylic acids, anethole, eugenol, methyl salicylate, limonene, ocimene, citronellol, methyl acetate, methyl eugenol, vanillin, thymol, spearmint oil, peppermint oil, lemon oil, orange oil, rosemary oil, cinnamon oil, eucalyptus oil and pimento oil alone or in combination.

If necessary, higher alcohols, higher fatty acids, shellac-ethylcellulose, ethylcellulose, carnauba wax, hydroxypropylmethylcellulose acetate succinate and solubilizing agents therefor may be used alone or in combination to effect control of the release of the active component from the base or to mask the odor of the active component.

The composition of the present invention comprise a base selected from those which have been confirmed in terms of their stability, and hence, which may be applied by various application methods without being limited to any specific one. For example, the ointment is suitable for any one of topical external application on the skin for the treatment of acne, urogenital application, oral application for the treatment of infectious periodontitis or the like.

In accordance with the present invention, it is also provided processes for preparing the composition of the invention.

The process of the invention is characterized in that a non-aqueous base is provided without any use of water in its preparation which would otherwise affect the stability of the active component. The process for preparing the composition of the present invention is described in detail below.

Three basic alternatives can be mentioned as methods for preparing the composition of the present invention, i.e., dispersion method, fusion method and slolubilizing method.

In the dispersion method, a homogeneous dispersion of the active component in a non-aqueous base is prepared by thoroughly grinding, pulverizing and kneading the active component, to make suitable the crystalline active component for topical administration. A preferred particle diameter of the active component is preferably 500 μm or less, normally 100 μm or less. For small scale production, the active component is mixed and thoroughly triturated with a portion of the base using an ointment slab and an ointment spatula or a mortar and a pestle. Subsequently, the rest of the base and other additives are added and trituration is continued until overall homogeneity is achieved. For large scale production, machines such as three roller machines, roll mills, kneaders, grinders or mixers are used. These machines may be used optionally under a reduced pressure or under heating. In such a case, the optimal stirring speed will be between 25 and 100 rpm and a preferred vacuum level ranges from 60 to 80 cmHg. A suitable heating temperature is between 35 to 60° C. depending on the stability of the active component. If necessary, the resulted particles may be screened.

In the fusion method, since the active component is readily soluble in water, and its activity is lowered by hydrolysis, the active component is first wet-triturated in a non-aqueous base such as a small amount of liquid paraffin. Subsequently, the other components are successively admixed in an order that increases the ability of the component to solubilize the active component, to thereby finally accomplish overall homogeneity. Fusion may be carried out under heating and stirring, if necessary. A suitable heating temperature is between 35 to 60° C. depending on the stability of the active component. An ointment jar and a water bath may be used for small scale production, while machines such as a three roller machine, grinders and mixers will be used in a water bath for large scale production. During the process, an optimal stirring speed is between 25 to 100 rpm and a preferred vacuum level is 60 to 80 cmHg. Particles may be filtered or screened, if necessary.

The solubilizing method comprises the use of a non-aqueous solvent compatible with the non-aqueous base since the active component is readily soluble in water and its activity is lowered by hydrolysis. For example, a solution of the active component in methanol or ethanol is kneaded with a non-aqueous base, optionally under heating or stirring. A suitable heating temperature is between 35 to 60° C. depending on the stability of the active component. The solution in which the active component has been dissolved is mixed and thoroughly triturated with a portion of the base, then further triturated with the rest of the base and other additives to provide overall homogeneity. Mixing or trituration is performed with an ointment slab and an ointment spatula or a mortar and a pestle for small scale production. For large scale production, a three roller machine, roller mills, kneaders, grinders and mixers or the like are used. These machines may be used optionally under reduced pressure and an optimal agitation speed is between 25 to 100 rpm and the vacuum level is preferably 60 to 80 cmHg. Optionally, particles may be filtered or screened.

The methods described above are p refer ably carried out under conditions which are free from not only water but also any other external factors which may potentially affect the stability of the active component. Such external factors include, for example, high temperatures, light and oxygen, which would all cause a deterioration in the active component.

The step of filling the composition into a container should also be carried out under conditions which are free from any of the stated external factors. Namely, the shape of the container should be capable of preventing contact with such external factors and also be able to properly maintain the stability of the active component of t he composition. Specific examples include bottles or jars made from glass, plastics and synthetic resins, or tubes made from metals, plastics and laminates. To seal the container, a screw cap is used to effect closure for bottles and jars, or folding a metal tube filled from its bottom end or contact-bonding a similarly filled plastic tube between hot plates, or contact-bonding a similarly filled laminate tube under heat such as high frequency or supersonic wave can also be employed.

The shape of the container may be selected depending on the intended use. Thus, in addition to the shapes mentioned above, the container may have a shape which enables, for example, direct application or injection of the composition at various body sites. One example is a container designed to discharge the composition by a piston-like rod from an injection cylinder or a syringe made from plastic or synthetic resin.

EXAMPLES

The following examples further illustrate the present invention using Compound 1 without, however, limiting the same thereto.

Example 1

| Component | % by weight |
| --- | --- |
| Compound 1 | 2.5[1)] |
| Hydrocarbon gel [2)] | 97.5 |

[1)] 2.0% as free anhydride (the same applies below)
[2)] Plastibase, available from Bristol-Myers Squibb Co. (the same applies below).

Compound 1 was mixed with hydrocarbon gel to overall homogeneity to give the desired composition.

Example 2

| Component | % by weight |
| --- | --- |
| Compound 1 | 6.2[3)] |
| Hydrocarbon gel | 93.8 |

[3)] 5.0% as free anhydride.

Compound 1 was mixed with hydrocarbon gel to overall homogeneity to give the desired composition.

Example 3

| Component | % by weight |
| --- | --- |
| Compound 1 | 12.4[(4] |
| Hydrocarbon gel | 87.6 |

[4)] 10.0% as free anhydride.

Compound 1 was mixed with hydrocarbon gel to overall homogeneity to give the desired composition.

Example 4

| Component | % by weight |
|---|---|
| Compound 1 | 2.5 |
| White petrolatum | 97.5 |

Compound 1 was mixed with white petrolatum to overall homogeneity to give the desired composition.

Example 5

| Component | % by weight |
|---|---|
| Compound 1 | 2.5 |
| Purified lanolin | 97.5 |

Compound 1 was mixed with purified lanolin to overall homogeneity to give the desired composition.

Example 6

| Component | % by weight |
|---|---|
| Compound 1 | 2.5 |
| Carmellose sodium | 2.0 |
| Hydrocarbon gel | 95.5 |

Compound 1 was mixed with a dispersion of carmellose sodium in hydrocarbon gel to give the desired composition. This composition is particularly suitable for oral application as a therapeutic agent for periodontal diseases.

Example 7

| Component | % by weight |
|---|---|
| Compound 1 | 2.5 |
| Xanthan gum | 2.0 |
| Hydrocarbon gel | 95.5 |

Compound 1 was mixed with a dispersion of xanthan gum in hydrocarbon gel to give the desired composition. This composition is suitable for oral application as a therapeutic agent for periodontal diseases.

Example 8

| Component | % by weight |
|---|---|
| Compound 1 | 2.5 |
| Liquid paraffin | 0.2 |
| Hydrocarbon gel | 97.3 |

Compound 1 was wet-kneaded with liquid paraffin and then mixed with hydrocarbon gel to overall homogeneity to give the desired composition.

Example 9

| Component | % by weight |
|---|---|
| Compound 1 | 2.5 |
| Ethanol | 0.1 |
| Hydrocarbon gel | 97.4 |

Hydrocarbon gel was added in portions into a solution of Compound 1 in ethanol and mixed to overall homogeneity to give the desired composition.

Stability test of penem-containing composition

A plastic container filled with a composition containing Compound 1 prepared according to the 5 formulations of Examples 1, and 4 to 7 was sealed with a screw cap. The container was stored at 40° C., 75% relative humidity (RH) for 1 month or 2 months or at room temperature for 1 month. Any observable change in the appearance of the composition was evaluated, and at the same time, the potency of the antibiotic was determined by high-performance liquid chromatography, from which the residual retention (%) to the initial potency was calculated.

Conditions for high-performance liquid chromatography were as follows. A stainless steel high-performance liquid chromatography column charged with octadecylsilylated silica gel was used. Column temperature was maintained at 40° C. The mobile phase consisted of Solution A containing 45 mM potassium dihydrogenphosphate, 5 mM sodium monohydrogenphosphate and 5 mM tetra-n-butylammonium bromide and Solution B comprising a 1:1 mixture of Solution A and acetonitrile. The mobile phase initially contained 16% of Solution B, then once analysis was started, Solution B was gradually increased to 70% over 54 minutes. The flow rate was controlled so that the retention time of Compound 1 was 24 minutes. The detector used was a UV spectrophotometer at a wavelength of 240 nm.

As controls, the following formulations using hydrophilic bases were also tested in the same manner.

Control 1

| Component | % by weight |
|---|---|
| Compound 1 | 2.5[1] |
| Hydrophilic ointment | 97.5 |

[1] 2.0% as free anhydride

Compound 1 was mixed with hydrophilic ointment to overall homogeneity to give the composition of Control 1.

Control 2

| Component | % by weight |
|---|---|
| Compound 1 | 2.5[1] |
| Absorptive ointment | 97.5 |

[1] 2.0% as free anhydride

Compound 1 was mixed with absorptive ointment to overall homogeneity to give the composition of Control 2. Results are shown in Table 1.

TABLE 1

| Composition No. (Control No.) | | | 1 | 2 | 3 | 4 | 5 | (1) | (2) |
|---|---|---|---|---|---|---|---|---|---|
| Formulation (% by weight) | Compound 1 | | 2.5 | 2.5 | 2.5 | 2.5 | 2.5 | 2.5 | 2.5 |
| | Hydrocarbon gel | | 97.5 | 95.5 | 95.5 | 0 | 0 | 0 | 0 |
| | White peterolatum | | 0 | 0 | 0 | 97.5 | 0 | 0 | 0 |
| | Purified lanolin | | 0 | 0 | 0 | 0 | 97.5 | 0 | 0 |
| | Hydrophilic ointment | | 0 | 0 | 0 | 0 | 0 | 97.5 | 0 |
| | Absorptive ointment | | 0 | 0 | 0 | 0 | 0 | 0 | 97.5 |
| | Carmellose sodium | | 0 | 2.0 | 0 | 0 | 0 | 0 | 0 |
| | Xanthan gum | | 0 | 0 | 2.0 | 0 | 0 | 0 | 0 |
| Stability test results | Initial appearance | | White Semisolid | Yellowish white Semisolid | Yellowish white Semisolid | Yellowish white Semisolid | Pale greenish yellow Semisolid | White Semisolid | White Semisolid |
| | Storage for 1 month at 40° C., 75% RH | Appearance after storage | Yellowish white Semisolid | Yellowish white Semisolid | Slightly pale yellow Semisolid | Slightly pale yellow Semisolid | Yellow Semisolid | Pale yellow Semisolid | Bright yellow Semisolid |
| | Storage for 2 months at 40° C., 75% RH | Appearance after storage | Yellowish white Semisolid | Yellowish white Semisolid | Slightly pale yellow Semisolid | Slightly pale yellow Semisolid | Yellow Semisolid | Pale yellow Semisolid | Dark reddish yellow Semisolid |
| | | Potency retention (%) | 100 | 97 | 100 | 100 | 92 | 0 | 0 |
| | Storage for 1 month at room temperature | Appearance after storage | White Semisolid | Yellowish white Semisolid | Yellowish white Semisolid | Yellowish white Semisolid | Pale greenish yellow Semisolid | Pale yellow Semisolid | Bright reddish yellow Semisolid |
| | | Potency retention (%) | 100 | 100 | 100 | 100 | 100 | 47 | 26 |

As shown in Table 1, combinations of Compound 1 with non-aqueous bases such as hydrocarbon gel, white petrolatum and purified lanolin provided stable compositions, and their stability was not adversely affected even by the addition of water-soluble polymer compounds such as carmellose sodium and xanthan gum as thickening agents. In contrast, when a water-absorbing ointment or hydrophilic ointment with hydrophilicity was used as a base, the active component was inactivated after storage at 40° C. for 2 months, or even after storage at room temperature for 1 month, and the properties of the composition were changed with a significant decrease in the residual titer of Compound 1 to generate many decomposition products including hydrolyzates, hydrolytic isomerization products and cleavage products of Compound 1.

Thus, the compositions in which Compound 1 was admixed into a non-aqueous bases according to the present invention were stable, and their stability was not affected even by addition of a water-soluble polymer compound.

A similar stability was observed when the composition according to the formulation of Example 1 was stored at room temperature for 3 years.

Advantageous effects of the invention

According to the present invention, very unstable penem antibiotics can be formulated into a stable composition by using hydrophobic polymer compounds as bases without the stability of the active component being compromised by further addition of water-soluble polymer compounds, to thereby provide antibacterial compositions which can be widely used in dermatological, ophthalmologic, otolaryngologic, dental/oral surgical and urogenital fields.

What is claimed is:

1. An antibacterial composition for topical administration comprising from 0.1 to 10% by weight, expressed as free anhydride on the basis of the entire composition, of (+)-(5R, 6S)-6-[(R)-1-hydroxyethyl]-7-oxo-3-[(R)-2-tetrahydrofuryl]-4-thia-1-azabicyclo[3.2.0]hepto-2-ene-2-carboxylic acid or a pharmaceutically acceptable salt thereof, the balance consisting essentially of a non-aqueous hydrophobic base selected from the group of compounds consisting of hydrocarbon gel, paraffin, liquid paraffin, white petrolatum, hydrophilic petrolatum, petrolatum, microcrystalline wax, plant oils, carnauba wax, beeswax, stearic acid, stearyl alcohol, cacao butter, cetanol, hard fat, white ointment, simple ointment, ceresin and the composition of aminoalkyl methacrylate copolymer E, aminoalkyl methacrylate copolymer RS, methacrylic acid copolymer L, methacrylic acid copolymer S, ethyl acrylate methyl methacrylate copolymer emulsion.

2. The composition of claim 1 wherein the hydrophobic compound is a hydrocarbon gel or white petrolatum.

3. The composition of claim 1 further comprising one or more additives selected from gelatinizers, thickening agents, viscosifiers, viscosity enhancers and elasticizers incorporated in the non-aqueous base.

4. The composition of claim 1 further comprising one or more of water-soluble or hydrophilic polymer compounds incorporated in the non-aqueous base.

5. The composition of claim 4 wherein the water-soluble or hydrophilic polymer compound is one or more members selected from the group consisting of carmellose, carmellose sodium, polyvinyl alcohol, polyvinyl pyrrolidone, polyacrylic acid, sodium polyacrylate, hydroxymethylcellulose, hydroxypropylcellulose, hydroxypropylmethylcellulose, hydroxyethylcellulose, hydroxyethylmethylcellulose, xanthan gum, tragacanth gum, guar gum, locust bean gum, arabic gum, chitosan, sodium alginate, starches, gelatins, hydrophobic hydroxypropylmethylcellulose, which is incorporated at 0.1 to 10% by weight on the basis of the composition.

6. The composition of claim 1 for dermatological external use.

7. The composition of claim 1 for dental external use.

* * * * *